(12) United States Patent
Lee et al.

(10) Patent No.: US 10,354,387 B2
(45) Date of Patent: Jul. 16, 2019

(54) MATERIAL CHARACTERIZATION FROM INFRARED RADIATION

(71) Applicant: Intel Corporation, Santa Clara, CA (US)

(72) Inventors: Chia-Hsun Lee, Santa Clara, CA (US); Haowei Liu, Fremont, CA (US); Amit Shahar, Sunnyvale, CA (US)

(73) Assignee: Intel Corporation, Santa Clara, CA (US)

( * ) Notice: Subject to any disclaimer, the term of this patent is extended or adjusted under 35 U.S.C. 154(b) by 192 days.

(21) Appl. No.: 15/443,751

(22) Filed: Feb. 27, 2017

(65) Prior Publication Data

US 2018/0249095 A1    Aug. 30, 2018

(51) Int. Cl.
| | | |
|---|---|---|
| G06T 7/11 | (2017.01) | |
| H04N 13/254 | (2018.01) | |
| G06K 9/20 | (2006.01) | |
| G01S 17/89 | (2006.01) | |
| G01S 17/46 | (2006.01) | |
| G01S 7/48 | (2006.01) | |
| G06K 9/62 | (2006.01) | |
| G06K 9/32 | (2006.01) | |

(52) U.S. Cl.
CPC ............ *G06T 7/11* (2017.01); *G01S 7/4802* (2013.01); *G01S 17/46* (2013.01); *G01S 17/89* (2013.01); *G06K 9/2018* (2013.01); *H04N 13/254* (2018.05); *G06K 9/209* (2013.01); *G06K 9/3233* (2013.01); *G06K 9/6267* (2013.01); *G06T 2207/10048* (2013.01)

(58) Field of Classification Search
CPC .... G06K 9/6267; G06K 9/2018; G06K 9/209; G06K 9/3233; G06T 2207/10048; G06T 7/11; H04N 5/33; H04N 13/254; G01S 7/4802; G01S 17/46; G01S 17/89
USPC .......................................................... 348/164
See application file for complete search history.

(56) References Cited

U.S. PATENT DOCUMENTS

| | | | |
|---|---|---|---|
| 8,189,050 B1 * | 5/2012 | Hughes .................. | H04N 5/33 348/162 |
| 2013/0069911 A1 * | 3/2013 | You ...................... | G06F 3/0416 345/175 |
| 2015/0261299 A1 * | 9/2015 | Wajs ...................... | G06F 3/011 726/19 |
| 2016/0048727 A1 * | 2/2016 | Zhang .................... | H04N 5/332 348/164 |

(Continued)

OTHER PUBLICATIONS

U.S. Appl. No. 15/200,062, entitled "Feature Characterization From Infrared Radiation", filed on Jul. 1, 2016, 38 pages.

*Primary Examiner* — Behrooz M Senfi
*Assistant Examiner* — Kathleen M Walsh
(74) *Attorney, Agent, or Firm* — Jordan IP Law, LLC (57) ABSTRACT

Systems, apparatuses, and/or methods to characterize a material. For example, and apparatus may include a pattern receiver to receive an IR pattern corresponding to non-uniform IR radiation that is to result from an interaction with a material, such as a translucent material. The apparatus may further include a characterizer to make a characterization of the material, such as a translucent material, based on the IR pattern. The characterization may differentiate the material, such as a translucent material, from one or more other materials, such as one or more other translucent materials.

20 Claims, 6 Drawing Sheets

(56) References Cited

U.S. PATENT DOCUMENTS

2017/0061663 A1\* 3/2017 Johnson ................. G06T 11/60
2017/0195654 A1\* 7/2017 Powers ................. G06T 7/521

\* cited by examiner

MATERIAL CHARACTERIZATION FROM INFRARED RADIATION

BACKGROUND

Surface characteristics may traditionally be ignored and/or treated as errors in depth camera imaging. For example, Time-of-Flight (ToF) cameras may assume that a reflection point is a constant (e.g., reflection of a Lambertian surface). However, not all surfaces are the same. In reality, part of light may enter an object. For certain objects (e.g., human skin, other translucent materials, etc.) light scatters under a surface. Accordingly, a traditional ToF calculation based on travel distance and duration may not be accurate, especially when object surface characteristics are ignored. Thus, there is considerable room for improvement to characterize a material.

BRIEF DESCRIPTION OF THE DRAWINGS

The various advantages of the embodiments will become apparent to one skilled in the art by reading the following specification and appended claims, and by referencing the following drawings, in which:

DESCRIPTION OF EMBODIMENTS

Figure 1:
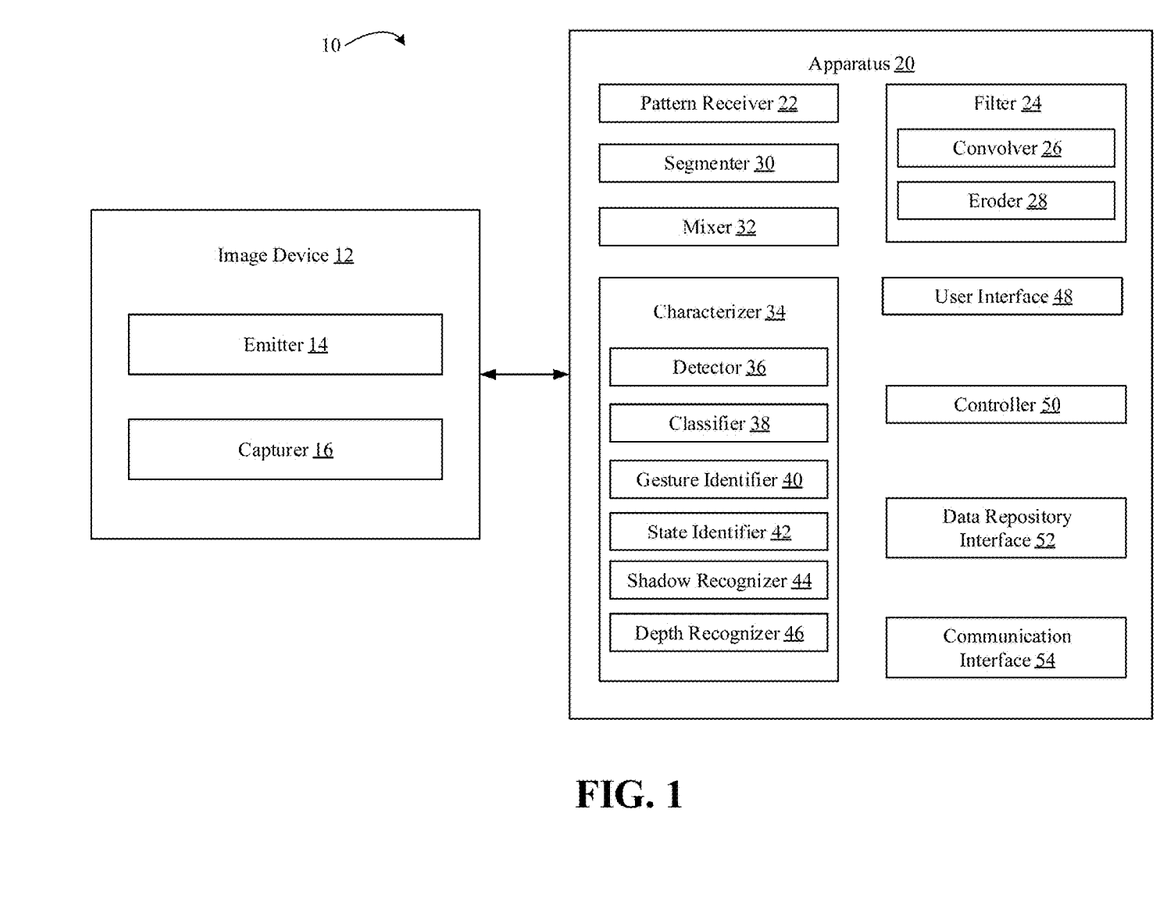
FIG. 1 is an illustration of an example of a system to characterize a material from infrared (IR) radiation according to an embodiment.

Turning now to FIG. 1, a system 10 is shown to characterize a material from infrared (IR) radiation according to an embodiment. The system 10 includes an image device 12 having an emitter 14 to emit electromagnetic radiation and a capturer 16 to capture radiation that is to result from an interaction with the material. The emitter 14 may emit electromagnetic radiation in one or more spectrums, such as the IR spectrum, the visible light spectrum, and so on. In addition, the emitter 14 may be located anywhere between two image sensors of the capturer 16, which may capture stereo images of a scene at different points of view. In one example, the image device 12 includes a three-dimensional (3D) camera such as an Intel® RealSense™ camera (Intel and RealSense are trademarks of Intel Corporation).

A scene captured by image sensors of the capturer 16 may include a material that interacts with radiation from the emitter 14. For example, a translucent material (TM) may allow radiation to pass through a surface thereof and/or may allow the image sensors of the capturer 16 to detect radiation has passed through when radiation is reflected back to the capturer 16. A TM may include, for example, any feature in a scene having skin such as a finger, a hand, an appendage, a face, and so on. A TM may also include an object in a scene such as food (e.g., fruit, meat, etc.), a polymer (e.g., plastic, acrylic, rubber, polyurethane, polyethylene glycol, polystyrene, etc.) a glass (e.g., flint glass, crown glass, etc.), an inanimate object (e.g., a table, a screen, a wall, etc.), a liquid (e.g. water, etc.), and so on. A non-TM material may not allow radiation to pass through a surface thereof. In addition, a non-TM material may reflect a substantial portion of radiation (e.g., cardboard, etc.) from the image device 12 and/or absorb a substantial portion of radiation (e.g., metal, etc.) from the image device 12.

Uniform IR radiation from the emitter 14 may, for example, traverse a lens of the image device 12 and be converted to non-uniform IR radiation having an IR pattern (e.g., a spatial IR pattern, a dotted IR pattern, etc.). Non-uniform IR radiation reflected by a material may provide an IR pattern that indicates different material optical properties relative to an IR pattern provided by non-uniform IR light that is absorbed (e.g., an undeterminable pattern). For example, an undeterminable IR pattern may appear, e.g., black indicating substantial absorption of non-uniform IR radiation. The undeterminable IR pattern may, for example, also include specks (e.g., dots, etc.) that appear, e.g., white indicating specular reflection from a surface of the non-TM material (e.g., holes that cause 180 degree reflection).

Moreover, non-uniform IR radiation that passes through a surface of a material and that is reflected may have a different IR pattern than non-uniform IR radiation that does not pass through a surface of a material, that is not absorbed, and that is reflected. In this regard, reflected non-uniform IR radiation may provide an IR pattern that is modified based on a sub-surface scattering effect caused from a composition of a material. Sub-surface scattering by a TM material such as skin may, for example, modify waveform properties (e.g., amplitude, etc.) of non-uniform IR radiation to form a softer and/or blurry IR pattern relative to a stronger and/or sharper IR pattern formed by non-uniform IR radiation reflected by a non-TM material such as cardboard, which may be substantially similar to the IR pattern leaving the image device 12. In addition, IR patterns among different TMs may be different due to respective TM sub-surface scattering effects that modify respective IR radiation waveform properties.

While material optical properties such as scattering, absorption, and reflection have been discussed, any other material optical properties may be involved (e.g., diffusion, translucence, etc.). Moreover, while waveform amplitude has been discussed, any other waveform properties may be involved (e.g., period, wavelength, etc.). Thus, the image sensors of the capturer 16 may be fed with a predetermined voltage (e.g., 5V) of electrical power to generate sensor signals based on waveform properties (e.g., amplitude, etc.). The generated sensor signals from the image sensors may be electrically transferred as analog sensor signals through a pull down resistor and converted to digital representation via an analog-to-digital converter.

A digital representation may include, for example, an IR image having IR patterns corresponding to one or more objects in a scene, wherein the IR patterns may include grayscale pixel values between a minimum value (e.g., 8-bit value, black pixel=0) and a maximum value (e.g., 8-bit value, white pixel=255). In one example, an IR pattern from a TM (e.g., TM IR pattern) may include grayscale pixel values that are relatively closer to a middle value (e.g., 8-bit value, middle gray pixel=128) and/or that are relatively farther from a minimum value and/or a maximum value. Notably, the grayscale pixel values may vary among TMs due to respective material optical properties that modulate respective waveform properties.

In another example, an IR pattern from a non-TM (e.g., non-TM IR pattern) may include grayscale pixel values that are substantially similar to grayscale pixel values of an IR pattern from the image device 12. Accordingly, for example, a TM IR pattern corresponding to skin may appear relatively softer and/or blurry compared to a non-TM IR pattern from a non-TM surface such as cardboard. A non-TM IR pattern may also be undeterminable, wherein a substantial portion of grayscale pixel values may be a minimum value and/or a maximum value (e.g, black, white, etc.) based on material optical properties (e.g., absorption, etc.) that modulate waveform properties.

Figure 2A:
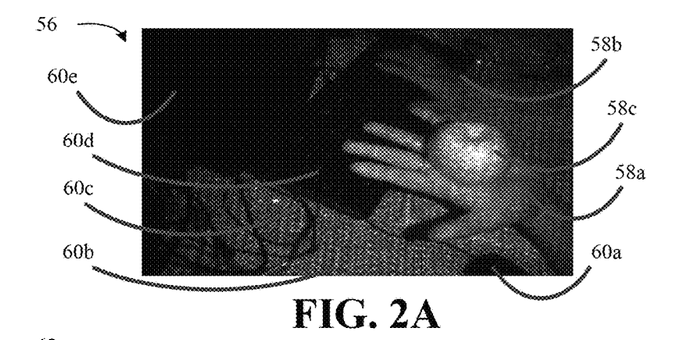
FIGS. 2A-2E are illustrations of example IR patterns to characterize a material according to an embodiment.

The system 10 further includes an apparatus 20 that may have logic (e.g., logic instructions, configurable logic, fixed-functionality logic hardware, etc.) configured to implement any of the herein mentioned processes including, for example, detecting a material, extracting a material, characterizing a material, processing data, and so on. In the illustrated example, the apparatus 20 includes a pattern receiver 22 to receive an IR pattern corresponding to IR radiation that has interacted with a material. For example, the pattern receiver 22 may obtain an IR pattern from the image device 12, a data repository, a communication interface, and so on. In one example, an IR pattern may include a raw IR pattern. As shown in FIG. 2A, for example, a raw IR image 56 includes raw TM IR patterns 58 (58a-58c) and raw non-TM IR patterns 60 (60a-60e).

Referring back to FIG. 1, the apparatus 20 further includes a filter 24 to generate an adjusted IR pattern from an IR pattern. For example, the filter 24 includes a convolver 26 to generate a sharpened IR pattern by modification of a pixel value in a raw IR pattern to a minimum value or a maximum value. The convolver 26 may, for example, apply a convolution kernel to an entire IR image including one or more IR patterns, having a pre-defined spatial rule such as an nxm sharpening kernel (e.g., a 3×3 sharpening kernel, where $A=a_{1,1}, a_{1,2}, a_{1,3}, a_{2,1}, a_{2,2}, a_{2,3}, a_{3,1}, a_{3,2}, a_{3,3}$, where $a_{1,1}, a_{1,3}, a_{3,1}, a_{3,3}=0, a_{1,2}, a_{2,1}, a_{2,3}, a_{3,2}=-2$, and $a_{2,2}=9$).

Figure 2B:
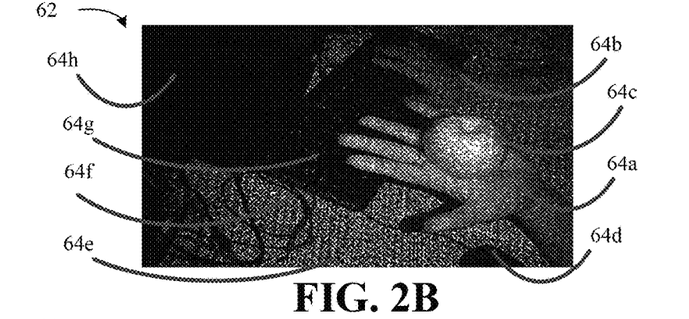

The result of the sharpening kernel may sharpen pixels by converting at least a part of gray pixels (e.g., a majority of gray pixels, substantially all gray pixels, etc.) to black pixels (e.g., 0) or white pixels (e.g., 255). In this regard, the sharpening kernel may not sharpen a grayscale pixel value to a maximum value or a minimum value when it is relatively closer to a middle value and may sharpen a grayscale pixel value to the maximum value or the minimum value when is relatively closer to the maximum value or the minimum value. As shown in FIG. 2B, for example, adjusted IR patterns 64 (64a-64h) in an adjusted IR image 62 illustrate that the raw non-TM IR patterns 60a-60e may be sharpened more than the raw TM IR patterns 58a-58c although the visible resolution of the raw TM IR patterns 58a-58c is enhanced in the adjusted IR patterns 64a-64c.

Referring back to FIG. 1, the filter 24 may remove at least a part of an adjusted IR pattern. Accordingly, an adjusted IR pattern may include a further adjusted IR pattern. For example, the filter 24 includes an eroder 28 to generate a further adjusted IR pattern from an adjusted IR pattern by removal of at least a part of the adjusted IR pattern. The eroder 28 may, for example, apply an erosion kernel having a pre-defined spatial rule (e.g., 3×3 kernel) to an entire IR image to substantially remove at least a part of an adjusted IR pattern based a neighborhood of pixel values including a minimum values and a maximum value. For example, the erosion kernel may be implemented to delete a pixel in an adjusted IR pattern (e.g., convert a white pixel to a black pixel) that neighbors a cluster of different pixels (e.g., a white pixel at $a_{2,2}$ surrounded by black pixels). The erosion kernel may not delete a grayscale pixel value if it is not a maximum value or a minimum value. Thus, erosion may result in a recognizable material (e.g., feature, etc.) via a remaining adjusted IR pattern in an adjusted IR image.

Figure 2C:
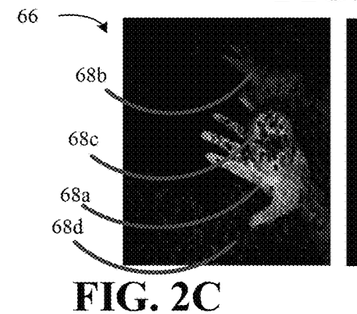

The eroder 28 may implement a plurality of iterations of erosion until a predetermined resolution threshold is met (e.g., until material/object contour appears, etc.). The number of iterations may be determined from factors such as a distance of a material to the image device 12, image device parameters such as IR gain and auto-exposure, and so on. In one example, three iterations of erosion may remove an IR pattern corresponding to a non-TM enough to, e.g., detect a TM, characterize a TM, etc. As shown in FIG. 2C, an adjusted IR image 66 includes further adjusted IR patterns 68 (68a-68d).

Figure 2D:
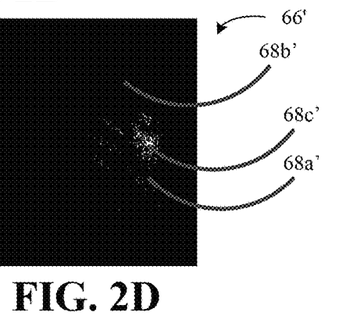
Figure 2E:
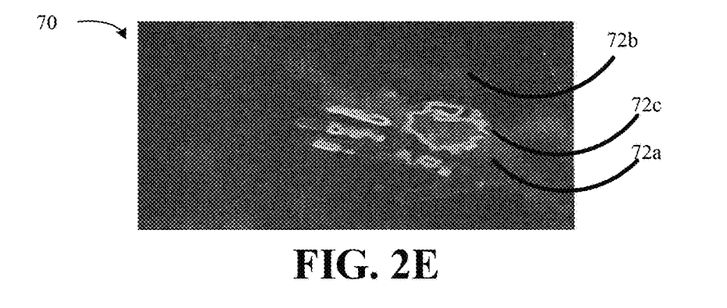

Pixels in a further adjusted IR pattern corresponding to a TM may become increasingly visibly faint with successive rounds of erosion. The pixels may not, however, be deleted. As shown in FIG. 2D, pixels in further adjusted IR patterns 68a'-68c' of adjusted IR image 66' for respective TMs become increasingly visibly faint with one further round of erosion while pixels in the further adjusted IR pattern 68d for a non-TM are deleted. The further adjusted IR patterns 68a'-68c', however, have pixel values that are available for processing (e.g., detection, extraction, recognition, rendering, etc.) regardless of whether they are visible in the adjusted IR image 66'. A heat map may, for example, provide a graphical representation of data where individual pixel values are represented as colors. As shown in FIG. 2E, a heat map 70 corresponding to the adjusted IR image 66' visually reveals the TMs via heat map IR patterns 72 (72a-72c).

Referring back to FIG. 1, the apparatus 20 includes a segmenter 30 to segment IR patterns based on a threshold (e.g., a material optical property threshold, etc.). In one example, the further IR pattern 68c' may correspond to a green apple that is less translucent than skin of a left pale skinned-hand and skin of a right pale-skinned hand corresponding to the further adjusted IR patterns 68a'-68b', respectively. The segmenter 30 may, in one example, apply a scattering threshold to segment the further adjusted IR patterns 68a'-68b', corresponding to relatively low scattering by skin, from the further adjusted IR pattern 68c', corresponding to relatively high scattering. The scattering threshold may include, for example, a predetermined grayscale pixel value. In one example, the predetermined grayscale pixel value may include a range of pixel values to which a predetermined number of pixels of an IR pattern may be compared. In this regard, the IR pattern may be segmented based on a preselected number of pixels of the IR pattern (e.g., of the predetermined number of pixels, etc.) that fall within and/or outside of the range.

Accordingly, for example, a pixel of an IR pattern above a particular grayscale value and/or the corresponding IR pattern may be sent to a high scattering path when a preselected number of pixels of the IR corresponding pattern are above a particular grayscale pixel value. In a further example, the predetermined grayscale pixel value may include a maximum and/or a minimum value. In this regard, for example, a pixel of an IR pattern and/or the corresponding IR pattern may be sent to a high scattering path when a preselected number of pixels of the corresponding IR pattern are relatively close to a maximum value, a pixel of an IR pattern and/or the corresponding IR pattern may be sent to a high absorption path when a preselected number of pixels of the corresponding IR pattern are relatively close to a minimum value, and so on. Thus, for example, pixels corresponding to the further adjusted IR patterns 68a'-68b' that fall below a threshold may be segmented to a low scattering path while pixels corresponding to the further adjusted IR pattern 68c' that are above the threshold may be segmented to a high scattering path. The segmenter 30 may also segment IR patterns based on any material optical property such as, for example, refraction, diffusion, reflection, and so on.

The apparatus 30 further includes a mixer 32 to mix IR patterns. In one example, the further adjusted IR patterns 68a'-68b' may be remixed with the further adjusted IR pattern 68c' after segmentation. Remixed IR patterns may be output in an image, such as the heat map 70. In addition, the mixer 32 may apply a weight to an IR pattern to further distinguish TMs in a remixed image. For example, the mixer 32 may apply a weight to the further adjusted IR pattern 68c' to further distinguish the image of the green apple from the image of the hands in the heat map 70. A weight of nine, for example, may be applied to pixels of the green apple to make one pixel value from the further adjusted IR pattern 68c' apply to nine pixels (1:9) in the heat map IR pattern 72c, and a weight of one may be to pixels of the skin to make one pixel value of from the further adjusted IR pattern 68a' apply to one pixel (1:1) in the heat map IR pattern 72a.

The apparatus 20 further includes a characterizer 34 to make a characterization of a material. The characterization may include differentiating between materials in a 3D space. In one example, the characterizer may differentiate a TM from another TM, a TM from a non-TM, a non-TM from another non-TM, etc. In the illustrated example, the characterizer 34 includes a detector 36 to detect whether a material is present based on an IR pattern. The detector 36 may, for example, use the raw TM IR patterns 58a-58c, the raw non-TM IR patterns 60a-60e, the adjusted IR patterns 64a-64h, etc., to determine whether a material is present. In one example, the detector 36 may use the raw TM IR pattern 58a in an object recognition process to determine that a material corresponds to a hand (e.g., recognize a palm in combination with five fingers, etc.). Thus, the output of the detector 36 may include a binary response (e.g., material present/not present, etc.), a relative description (e.g., five materials present, less than ten materials present, etc.), and so on. The output of the detector 36 may further include a general description (e.g., hand present, fruit present, etc.).

The characterizer 34 further includes a classifier 38 to classify a material, wherein classification of the material may provide a specific description of the material. For example, a general description (e.g., hand present, etc.) may be refined using the classifier 38 to classify the material as a specific type of material (e.g. skin of a hand is present, prosthetic present, etc.). The classifier 38 may, for example, use the raw TM IR patterns 58a-58c, the adjusted IR patterns 64a-64c, etc., to determine that a TM is present based on relatively close proximity of grayscale values to middle gray, based on a predetermined absence of grayscale values having a minimum value and/or a maximum value, and so on. The classifier 38 may, for example, use the raw TM IR pattern 58a to determine that a relatively soft and/or blurry pattern is present and classify a material as a TM. The classifier 38 may further confirm whether a non-TM material is present based on IR patterns that substantially match the IR pattern from the image capture device 12 (e.g., cardboard present when IR patterns match, etc.). The classifier 38 may also confirm a non-TM is present based on an undeterminable IR pattern. For example, the classifier 38 may use the raw non-TM IR pattern 60a to classify a material as a non-TM.

The classifier 38 may also compare a new IR pattern with a reference IR pattern (e.g., reference grayscale values, etc.) to identify a material. For example, a training process may generate reference IR patterns for a plurality of TMs which when compared to a new IR pattern identifies a particular material for the new IR pattern when there is a match (e.g., a predetermined match confidence on a pairwise pixel-by-pixel match basis for a predetermined part of an IR pattern, etc.). In this regard, capture data may be evaluated to normalize capture environments. Capture data may include, for example, 3D shape of an object, z-proximity of an object, wavelength of a light source, and so on. In one example, a user may be instructed to move the image device 12 and/or an object to normalize capture environments. In another example, the classifier 38 may obtain a best reference IR pattern based on the capture data for the new IR pattern.

Filtering may further enhance distinctions between TMs and/or non-TMs. For example, the classifier 38 may use the further adjusted IR pattern 68a to confirm that a TM is present, use the further adjusted pattern 68b to determine that another TM present, and/or use the absence of further adjusted IR patterns corresponding to adjusted IR patterns (e.g., after filtering, etc.) to confirm that non-TMs are present. Materials may be further characterized based optical properties of materials. For example, the classifier 38 may qualitatively and/or quantitatively determine one or more optical properties of a material. A material optical property may include, for example, relative refractive index (p), Lambertian reflection (q), relative diffusion constant (r), and so on. Thus, the image device 12 may be implemented to obtain capture data for objects in a 3D scene as 3D points with respective color information (e.g., x, y, z, R, G, B) and, additionally, obtain surface characteristics for a 3D point (e.g., p, q, r, s, etc.). Part and/or all of the data set (e.g., x, y, z, R, G, B, p, q, r, s, etc.) may be used for processing (e.g., object detection, object recognition, material identification, image generation, food safety, etc.).

Figure 3:
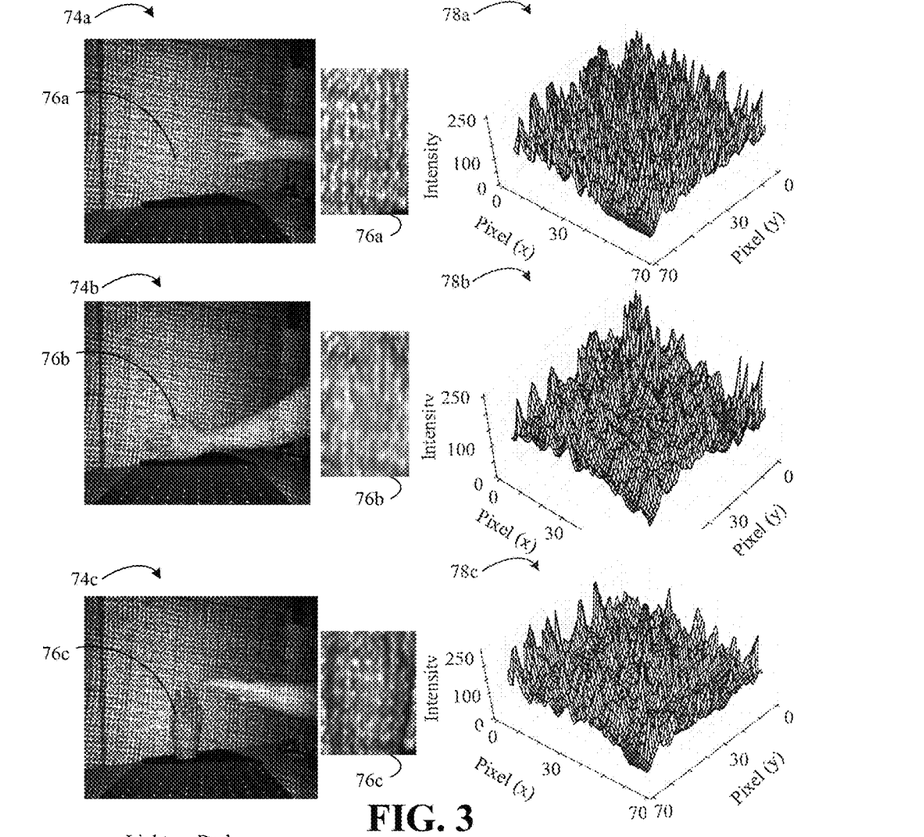
FIG. 3 are illustrations of example IR patterns and example waveforms to characterize a material according to an embodiment.

As shown in FIG. 3, for example, raw IR images 74 (74a-74c) may be captured using a left imager of a depth camera (e.g., Intel® RealSense™ R200). Different materials may have different ways of interacting with IR radiation emitted from the left imager, and waveforms that carry energy onto surfaces of materials may be changed (e.g., shape modified, amplitude modified, etc.) in different ways. Regions of interest (ROI) 76 (76a-76c) (e.g, 70 (x) pixels× 70 (y) pixels) illustrate example changes. The raw IR pattern of the ROI 76a has relatively sharp and/or strong black and white areas compared to the raw IR pattern of to the ROI 76b, which has relatively blurred and/or weak gray areas due to the material optical properties of a real human hand in the ROI 76b. The raw IR pattern of the ROI 76c has also changed compared to the "no object" pattern of the ROI 76a, and has relatively sharp and/or strong gray areas due to the material optical properties of a prosthetic hand (e.g., a rubber hand) in the ROI 76c.

The absence of an object in front of a cardboard material in the ROI 76a causes a waveform, shown as two-dimensional (2D) waveform 78a, reflected from the cardboard material back to the left imager to be substantially the same as the waveform that was emitted from the depth camera. The presence of the hand in front of the cardboard material in the ROI 76b causes a waveform, shown as a 2D waveform 78b, reflected from the real hand back to the left imager to change compared to the waveform that was emitted from the depth camera. In this regard, skin of the real hand is translucent and modifies the IR pattern emitted from the depth camera due to sub-scattering effects.

The presence of the prosthetic hand in in front of the cardboard material in the ROI 76c causes a waveform, shown as 2D waveform 78c, that is reflected from the prosthetic hand back to the left imager to change compared to the waveform that was emitted from the depth camera. In addition, rubber may be less translucent than skin and/or absorb more IR radiation with less scattering than the skin of the hand. Thus, the waveforms 78b-78c may be different and/or distinguished. In the illustrated example, the 2D waveforms 78a, 78c show that the cardboard reflects more IR radiation back to the depth camera than the prosthetic hand and therefore intensity (e.g., grayscale, 0-255) is greater for the waveform 78a. The prosthetic hand, however, visually appears as a lighter color in RGB than the cardboard but absorbs more IR radiation than the cardboard. The 2D waveforms 78a-78b show that the cardboard also reflects more IR radiation back to the depth camera than the skin of the real hand and therefore intensity is greater for the waveform 78a.

Accordingly, the classifier 38 may determine the relative translucence, absorbance, diffusion, reflection, scattering, etc., for a material based on an IR pattern and/or a waveform. In one example, translucence may be proportional to scattering and/or inversely proportional to reflection. Material optical properties may also be quantitatively determined based on an IR pattern. In one example, the diffusion constant (D) may be set equal to ⅓ $\sigma'_t$, wherein $\sigma'_t$ is the reduced extension coefficient (e.g., the extension coefficient may be the imaginary part of the complex index of refraction, which also related to light absorbance). Given an approximation of an index of refraction (e.g., calculated, based on an IR pattern match with a reference IR pattern associated with a known index of refraction, etc.), one or more other optical properties may be determined.

Figure 4:
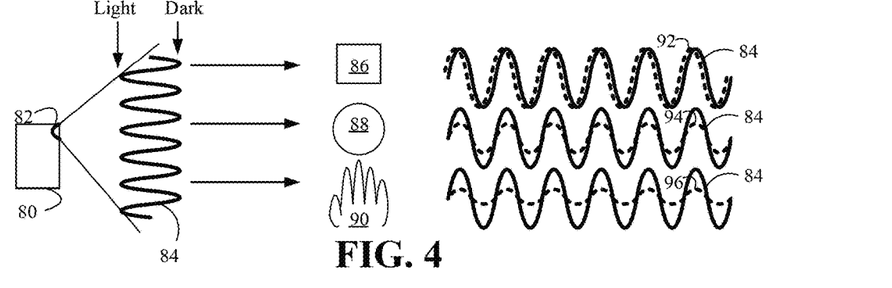
FIG. 4 are illustrations of example waveforms to characterize a material according to an embodiment.

As shown in FIG. 4, an emitter 82 of a depth camera 80 emits an IR pattern 84 including light and dark portions, which interacts with a non-TM 86 (e.g., a cardboard box), a TM 88 (e.g., a green apple), and a TM 90 (e.g., human skin). An index of refraction may be determined based on, for example, the relation Wi-Wo=3D shape+signature, wherein Wi is indecent wave, Wo is observed wave, 3D shape is determined by data from the depth camera 80 and may be zero if flat, and signature is a signature wave for a material which may be zero for a non-TM. In the illustrated example, one-dimensional (1D) waveforms illustrate that a signature wave 92 for the non-TM material 86 is substantially the same as the waveform 84 from the depth camera 80. In this regard, an index of refraction may be close to zero if light is fully reflected (e.g., a mirror, etc.). In addition, an index of refraction that is less than one may indicate that a material includes reflective properties on a surface thereof.

Accordingly, when the non-TM 86 is, e.g., flat (or has a flat side) and there is light reflectance equal to light emission (e.g., indicated by Wo, a signature wave, etc.), there is no scattering and the index of refraction may be zero. In this case, the classifier 38 may classify the non-TM 86 based on corresponding material optical properties (e.g., cardboard, non-TM, etc.). Signature waves 94, 96 however, are different than the waveform 84 from the depth camera 80. For example, amplitude of the signature wave 94 is larger than amplitude of the signature wave 92, which are each lower than amplitude of the waveform 84. The green apple reflects more light than the hand in the illustrated example, and the hand scatters more light than the green apple in the illustrated example. Thus, the classifier 38 may classify the TMs 88, 90 based on the respective material optical properties (e.g., TM, skin, green apple, fruit, etc.) determined from the respective signature waves 94, 96.

Characterization of a material may further include a gesture involving a material. Retuning back to FIG. 1, the characterizer 34 includes a gesture identifier 40 to determine whether a gesture is made based on an IR pattern. For example, a TM material may include skin of a feature that may be involved in a gesture (e.g., point, etc.). Characterization of a TM may also include a state involving a material. In the illustrated example, the characterizer 34 includes a state identifier 42 to identify a state involving a material based on an IR pattern. For example, a material may currently be in contact with an object (e.g., a surface, a hand, etc.) and the state identifier 42 may identify the contact state. Other states may include, for example, a motion state, motionless state, a pressing state, a resting state, a gesture state, a typing state, an approaching state, and so on.

Additionally, the state identifier 42 may determine the state of a material for use. For example, prior knowledge regarding an object in 3D space may be used to determine whether a state of food is suitable for consumption. In this regard, meat, fruit, milk, etc., may provide scattering effects that provide IR patterns indicating suitability for consumption. Thus, a deviation from such IR patterns may indicate that the food is spoiled, is unsuitable for consumption, etc. In another example, the object may include a polymer coating (e.g., acrylic, etc.) corresponding to an IR pattern that indicates suitability of the object for a particular environment (e.g., outdoor use, indoor use, etc.).

The characterizer 34 further includes a shadow recognizer 44 to recognize a shadow associated with a material. The shadow recognizer 44 may, for example, determine a shadow concentration between two or more IR patterns. Accordingly, a touch event involving a material may be determined based on, for example, the shadow concentration. The shadow concentration may, for example, decrease when a material moves towards another material and away from the emitter 14. In addition, proximity involving a material may be determined based on, for example, the shadow concentration. The shadow concentration may, for example, be used to determine that a specific number of black pixels from the shadow concentration indicate a specific distance of a material relative to another material. A touch event and/or proximity may, however, be determined using any sensor data (e.g., pressure associated with a user feature, RBG values, etc.). In addition, the detector 36 and/or the classifier 38 may use capture data (e.g., shadow data, depth data, etc.) to detect and/or characterize a material.

The characterizer 34 further includes a depth recognizer 46 to recognize a depth of a material in 3D space. Accordingly, high quality 3D z-proximity spatial data for a material may be used to determine a position of a material relative to one or more other TMs in 3D space, etc. In this regard, user experience may be enhanced in an augmented reality (AR) environment, a virtual reality (VR) environment, etc., when the depth data is used with an IR pattern to render images in a graphics application. In the illustrated example, the apparatus 20 further includes a user interface 48 to provide a representation of data associated with a material. For example, the user interface may be rendered via a display screen or projected (e.g., in air, onto a surface, etc.) to render IR images, heat map images (e.g., heat maps, etc.), detection results, characterization results, and so on.

In one example, an IR pattern may be used to render images in a graphics application (e.g., by a shader). An IR pattern may, for example, be used to characterize a surface of a material for realistic render of the material. On a render pass, scattering parameters such as reduced extension coefficient, absorption, index of refraction, etc., may be used to realistically render a TM. The user interface 48 may, however, provide other sensory representations of data associated with a material. For example, the user interface 48 may provide an auditory and/or a tactile representation of data. In one example, the user interface 48 may provide an audio notification that a material is present (e.g., object present, skin present, prosthetic present, TM present, non-TM present, etc.), that a material is not suitable for use (e.g., spoiled fruit, etc.), and so on.

The apparatus 20 further includes a controller 50 to generate control function data for a function of a computing platform based on the characterization of the material. The computing platform may include, for example, a laptop, personal digital assistant (PDA), media content player, mobile Internet device (MID), any smart device such as a wireless smart phone, smart tablet, smart TV, smart watch, computer server, gaming platform, and so on. In one example, the computing platform may be separate from the image device 12 and/or the apparatus 20. In another example, the computing platform may be integral with the image device 12 and/or the apparatus 20.

The controller 50 may, for example, generate control function data to control operation of a drone (e.g., a vehicle, etc.), a surgical instrument, a smart device, and so on. In one example, the control data may control selection of characters from a keyboard associated with a smart device that may be projected onto a surface, that may be disposed in air over the surface in a real environment, in an AR environment, and so on. In a further example, the control data may control features of a game to add responsiveness when a user feature is moving in 3D space rather than responsiveness only when the user feature is in contact with a surface. For example, movement towards a surface may be correlated to movement in a game to enhance user experience. The controller may also control a shipment of goods (e.g., speed up shipment a food shipment that is in danger of spoiling, re-route a shipment with spoiled food, etc.).

The apparatus 20 further includes a data repository interface 52 that may interface with memory (e.g., cache, random access memory, etc.), with a hard drive (e.g., on-platform storage, removable storage, etc.), and so on. The apparatus 20 may also include a communication interface 54 that may interface with communication functionality for a wide variety of purposes such as, for example, cellular telephone (e.g., Wideband Code Division Multiple Access/W-CDMA (Universal Mobile Telecommunications System/UMTS), CDMA2000 (IS-856/IS-2000), etc.), WiFi (Wireless Fidelity, e.g., Institute of Electrical and Electronics Engineers/IEEE 802.11-2007, Wireless Local Area Network/LAN Medium Access Control (MAC) and Physical Layer (PHY) Specifications), LiFi (Light Fidelity, e.g., Institute of Electrical and Electronics Engineers/IEEE 802.15-7, Wireless Local Area Network/LAN Medium Access Control (MAC) and Physical Layer (PHY) Specifications), 4G LTE (Fourth Generation Long Term Evolution), Bluetooth (e.g., Institute of Electrical and Electronics Engineers/IEEE 802.15.1-2005, Wireless Personal Area Networks), WiMax (e.g., IEEE 802.16-2004, LAN/MAN Broadband Wireless LANS), Global Positioning System (GPS), spread spectrum (e.g., 900 MHz), NFC (Near Field Communication, ECMA-340, ISO/IEC 18092), and other radio frequency (RF) purposes. Thus, the apparatus 20 may utilize the data repository interface 52 and/or the communication interface 54 to provide access to data to/from one or more components of the system 10.

Accordingly, material characterizations may be made relatively efficiently, which may in turn provide relatively efficient processing. For example, material detection and/or material extraction may be relatively efficient using IR patterns. Raw IR images and/or filtered IR images (e.g., convolved IR images) may be used to detect materials. In addition, material detection and/or material extraction may be refined to TM detection and/or TM extraction. TM detection and/or TM extraction may further be refined to skin/non-skin determinations. In addition, absence of data in a filtered image (e.g., IR images, heat maps, etc.) may indicate whether non-TMs are present. Moreover, a wide array of applications include, for example, graphics rendering, security assurance (e.g., check-point security, etc.), food quality assurance, hazard material detection, etc.

While examples have provided various components of the system 10 for illustration purposes, it should be understood that one or more components of the image device 12 and/or the apparatus 20 may reside in the same and/or different physical and/or virtual locations, may be combined, omitted, bypassed, re-arranged, and/or be utilized in any order. In one example, one or more components of the image device 12 may physically reside on the same computing platform as one or more components of the apparatus 20. In another example, one or more components of the image device 12 and/or the apparatus 20 may be distributed among various computing platforms to provide distributed user feature characterization. Moreover, any or all components of the image device 12 and/or the apparatus 20 may be automatically implemented (e.g., without human intervention, etc.). For example, the filter 24 may automatically generate an adjusted IR pattern.

Figure 5:
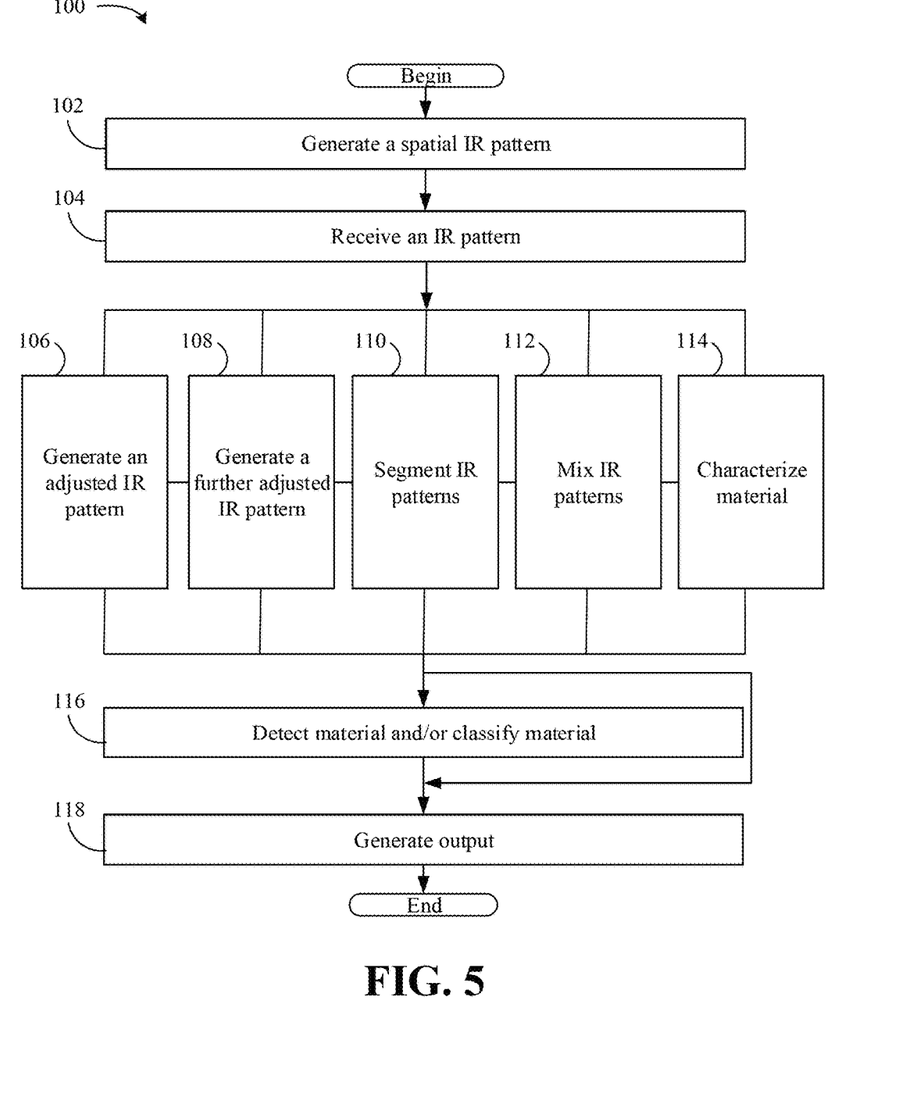
FIG. 5 is an illustration of an example of a method to characterize a material according to an embodiment.

Turning now to FIG. 5, a method 100 is shown to characterize a user feature from IR radiation according to an embodiment. The method 100 may be implemented as a module or related component in a set of logic instructions stored in a non-transitory machine- or computer-readable storage medium such as random access memory (RAM), read only memory (ROM), programmable ROM (PROM), firmware, flash memory, etc., in configurable logic such as, for example, programmable logic arrays (PLAs), field programmable gate arrays (FPGAs), complex programmable logic devices (CPLDs), in fixed-functionality hardware logic using circuit technology such as, for example, application specific integrated circuit (ASIC), complementary metal oxide semiconductor (CMOS) or transistor-transistor logic (TTL) technology, or any combination thereof.

For example, computer program code to carry out operations shown in the method 100 may be written in any combination of one or more programming languages, including an object oriented programming language such as JAVA, SMALLTALK, C++ or the like and conventional procedural programming languages, such as the "C" programming language or similar programming languages. Additionally, logic instructions might include assembler instructions, instruction set architecture (ISA) instructions, machine instructions, machine dependent instructions, microcode, state-setting data, configuration data for integrated circuitry, state information that personalizes electronic circuitry and/or other structural components that are native to hardware (e.g., host processor, central processing unit/CPU, microcontroller, etc.).

Illustrated processing block 102 provides for generating a spatial IR pattern. Block 102 may, for example, emit IR radiation through a camera lens to form an IR pattern (e.g., dotted IR pattern) and IR radiation that results from an interaction with a material may be captured. The IR radiation may include non-uniform IR radiation that is reflected, that is scattered, and so on. Illustrated processing block 104 provides for receiving an IR pattern. Block 104 may, for example, obtain an IR image having IR patterns corresponding to materials in a scene. In one example, IR patterns may include grayscale pixel values between a minimum value (e.g., 8-bit value, black pixel=0) and a maximum value (e.g., 8-bit value, white pixel=255). An IR pattern may include an undeterminable IR pattern that has a substantial amount of pixels at a minimum and/or a maximum value. The IR image may also include a heat map.

Illustrated processing block 106 provides for generating an adjusted IR pattern from an IR pattern. Block 106 may, for example, apply a convolution kernel such as a sharpening kernel (e.g., nxm kernel) to generate an adjusted IR pattern by modification of a pixel value in an IR pattern to a minimum value (e.g., 8-bit value=0) or a maximum value (e.g., 8-bit value=255). In addition, illustrated processing block 108 may apply an erosion kernel (e.g., nxm kernel) to generate a further adjusted IR pattern from an adjusted IR pattern by removal of at least a part of a sharpened IR pattern from the adjusted IR pattern based on a neighborhood of pixel values including the minimum value and the maximum value (e.g., until a predetermined resolution threshold is met). Block 108 may implement a plurality of iterations of erosion until the predetermined resolution is met.

Illustrated processing block 110 provides for segmenting IR patterns. Block 110 may, for example, segment further adjusted IR patterns based on a material optical property threshold. For example, block 110 may apply a scattering threshold to segment IR patterns to a low scattering path and to a high scattering path. Block 110 may also segment IR patterns based on any material optical property such as refraction, diffusion, absorption, reflection, and so on. Illustrated processing block 112 provides for mixing segmented IR patterns. Block 112 may, for example, remix segmented IR patterns (e.g., segmented further adjusted IR patterns, etc.). Block 112 may apply a weight to IR patterns (e.g., to segmented further adjusted IR patterns, etc.). The weight may, for example, further distinguish materials by highlighting particular materials in an output image using the weight.

Illustrated processing block 114 provides for making a characterization of a material. Block 114 may, for example, differentiate a TM from another TM, a TM from a non-TM, a non-TM from another non-TM, etc. Illustrated processing block 116 provides for detecting a material. Block 116 may, for example, detect whether a TM is present in a 3D space based on an IR pattern. For example, block 116 may utilize a raw IR pattern, an adjusted IR pattern, etc., to detect whether a TM is present. Block 116 may use corresponding IR patterns to detect two or more materials in a same 3D space.

Block 116 further provides for classifying a material. For example, block 116 may classify a TM as a specific TM based on an IR pattern. In one example, a general description (e.g., hand present) may be refined using block 116 to classify the material as a specific type of material (e.g. skin of a hand is present, prosthetic present, etc.). Block 116 may also classify one or more other TMs based on respective IR patterns in an IR image. For example, block 116 may classify one or more other TMs as specific TMs (e.g., green apple, skin, etc.). Block 116 may further classify a material as a non-TM via a respective IR pattern (e.g., undeterminable pattern, matching pattern to emitting pattern, etc.).

Block 116 further provides for determining a material optical property of a material to classify the material as a specific material. Block 116 may, for example, compare a new IR pattern with a reference IR pattern, may qualitatively and/or quantitatively determine one or more optical properties of a material, and so on.

Illustrated processing block 118 provides for generating an output. For example, block 118 may control an operation of a computing platform based on a characterization of a material. Block 118 may further generate an output image (e.g., an IR image, a heat map, etc.). Block 118 may, for example, provide scattering parameters such as reduced extension coefficient, absorption, index of refraction, etc., to realistically render a TM in a graphics application. Block 118 may, for example, provide an auditory and/or a tactile representation of data (e.g., output a notification) for a wide array of implementations such as food safety, security assurance, hazard prevention, and so on. Block 118 may, for example, provide an output related to material detection (e.g., present/not present), material extraction (e.g., feature extraction, etc.), material recognition (e.g., skin present, TM present, non-TM present, cardboard present, metal present, etc.), and so on.

While independent blocks and/or a particular order has been shown for illustration purposes, it should be understood that one or more of the blocks of the method 100 may be combined, omitted, bypassed, re-arranged, and/or flow in any order. In addition, any or all blocks of the method 100 may include further techniques, including techniques to recognize a state of a material, a shadow associated with a material, depth of a material in 3D space, and so on. Moreover, any or all blocks of the method 100 may be automatically implemented (e.g., without human intervention, etc.). For example, block 106 may automatically generate an adjusted IR pattern.

Figure 6:
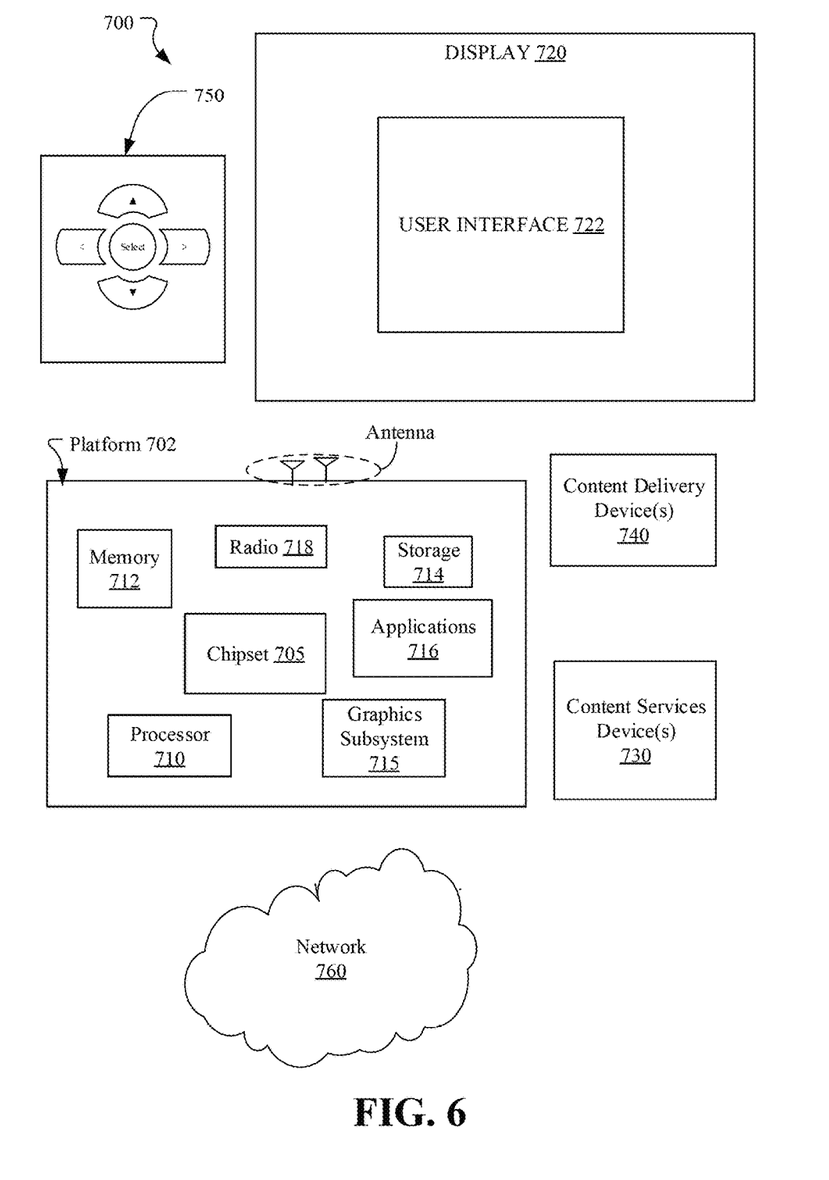
FIG. 6 is a block diagram of an example of a system having logic according to an embodiment.

FIG. 6 illustrates an embodiment of a system 700. In embodiments, system 700 may be a media system although system 700 is not limited to this context. For example, system 700 may be incorporated into a personal computer (PC), laptop computer, ultra-laptop computer, tablet, touch pad, portable computer, handheld computer, palmtop computer, personal digital assistant (PDA), cellular telephone, combination cellular telephone/PDA, television, smart device (e.g., smart phone, smart tablet or smart television), mobile internet device (MID), messaging device, data communication device, and so forth.

In embodiments, the system 700 comprises a platform 702 coupled to a display 720 that presents visual content. The platform 702 may receive video bitstream content from a content device such as content services device(s) 730 or content delivery device(s) 740 or other similar content sources. A navigation controller 750 comprising one or more navigation features may be used to interact with, for example, platform 702 and/or display 720. Each of these components is described in more detail below.

In embodiments, the platform 702 may comprise any combination of a chipset 705, processor 710, memory 712, storage 714, graphics subsystem 715, applications 716 and/or radio 718 (e.g., network controller). The chipset 705 may provide intercommunication among the processor 710, memory 712, storage 714, graphics subsystem 715, applications 716 and/or radio 718. For example, the chipset 705 may include a storage adapter (not depicted) capable of providing intercommunication with the storage 714.

The processor 710 may be implemented as Complex Instruction Set Computer (CISC) or Reduced Instruction Set Computer (RISC) processors, x86 instruction set compatible processors, multi-core, or any other microprocessor or central processing unit (CPU). In embodiments, the processor 710 may comprise dual-core processor(s), dual-core mobile processor(s), and so forth.

The memory 712 may be implemented as a volatile memory device such as, but not limited to, a Random Access Memory (RAM), Dynamic Random Access Memory (DRAM), or Static RAM (SRAM).

The storage 714 may be implemented as a non-volatile storage device such as, but not limited to, a magnetic disk drive, optical disk drive, tape drive, an internal storage device, an attached storage device, flash memory, battery backed-up SDRAM (synchronous DRAM), and/or a network accessible storage device. In embodiments, storage 714 may comprise technology to increase the storage performance enhanced protection for valuable digital media when multiple hard drives are included, for example.

The graphics subsystem 715 may perform processing of images such as still or video for display. The graphics subsystem 715 may be a graphics processing unit (GPU) or a visual processing unit (VPU), for example. An analog or digital interface may be used to communicatively couple the graphics subsystem 715 and display 720. For example, the interface may be any of a High-Definition Multimedia Interface (HDMI), DisplayPort, wireless HDMI, and/or wireless HD compliant techniques. The graphics subsystem 715 could be integrated into processor 710 or chipset 705. The graphics subsystem 715 could be a stand-alone card communicatively coupled to the chipset 705. In one example, the graphics subsystem 715 includes a noise reduction subsystem as described herein.

The graphics and/or video processing techniques described herein may be implemented in various hardware architectures. For example, graphics and/or video functionality may be integrated within a chipset. Alternatively, a discrete graphics and/or video processor may be used. As still another embodiment, the graphics and/or video functions may be implemented by a general purpose processor, including a multi-core processor. In a further embodiment, the functions may be implemented in a consumer electronics device.

The radio 718 may be a network controller including one or more radios capable of transmitting and receiving signals using various suitable wireless communications techniques. Such techniques may involve communications across one or more wireless networks. Exemplary wireless networks include (but are not limited to) wireless local area networks (WLANs), wireless personal area networks (WPANs), wireless metropolitan area network (WMANs), cellular networks, and satellite networks. In communicating across such networks, radio 718 may operate in accordance with one or more applicable standards in any version.

In embodiments, the display 720 may comprise any television type monitor or display. The display 720 may comprise, for example, a computer display screen, touch screen display, video monitor, television-like device, and/or a television. The display 720 may be digital and/or analog. In embodiments, the display 720 may be a holographic display. Also, the display 720 may be a transparent surface that may receive a visual projection. Such projections may convey various forms of information, images, and/or objects. For example, such projections may be a visual overlay for a mobile augmented reality (MAR) application. Under the control of one or more software applications 716, the platform 702 may display user interface 722 on the display 720.

In embodiments, content services device(s) 730 may be hosted by any national, international and/or independent service and thus accessible to the platform 702 via the Internet, for example. The content services device(s) 730 may be coupled to the platform 702 and/or to the display 720. The platform 702 and/or content services device(s) 730 may be coupled to a network 760 to communicate (e.g., send and/or receive) media information to and from network 760. The content delivery device(s) 740 also may be coupled to the platform 702 and/or to the display 720.

In embodiments, the content services device(s) 730 may comprise a cable television box, personal computer, network, telephone, Internet enabled devices or appliance capable of delivering digital information and/or content, and any other similar device capable of unidirectionally or bidirectionally communicating content between content providers and platform 702 and/display 720, via network 760 or directly. It will be appreciated that the content may be communicated unidirectionally and/or bidirectionally to and from any one of the components in system 700 and a content provider via network 760. Examples of content may include any media information including, for example, video, music, medical and gaming information, and so forth.

The content services device(s) 730 receives content such as cable television programming including media information, digital information, and/or other content. Examples of content providers may include any cable or satellite television or radio or Internet content providers. The provided examples are not meant to limit embodiments.

In embodiments, the platform 702 may receive control signals from a navigation controller 750 having one or more navigation features. The navigation features of the controller 750 may be used to interact with the user interface 722, for example. In embodiments, the navigation controller 750 may be a pointing device that may be a computer hardware component (specifically human interface device) that allows a user to input spatial (e.g., continuous and multi-dimensional) data into a computer. Many systems such as graphical user interfaces (GUI), and televisions and monitors allow the user to control and provide data to the computer or television using physical gestures.

Movements of the navigation features of the controller 750 may be echoed on a display (e.g., display 720) by movements of a pointer, cursor, focus ring, or other visual indicators displayed on the display. For example, under the control of software applications 716, the navigation features located on the navigation controller 750 may be mapped to virtual navigation features displayed on the user interface 722, for example. In embodiments, the controller 750 may not be a separate component but integrated into the platform 702 and/or the display 720. Embodiments, however, are not limited to the elements or in the context shown or described herein.

In embodiments, drivers (not shown) may comprise technology to enable users to instantly turn on and off the platform 702 like a television with the touch of a button after initial boot-up, when enabled, for example. Program logic may allow the platform 702 to stream content to media adaptors or other content services device(s) 730 or content delivery device(s) 740 when the platform is turned "off." In addition, chipset 705 may comprise hardware and/or software support for 5.1 surround sound audio and/or high definition 7.1 surround sound audio, for example. Drivers may include a graphics driver for integrated graphics platforms. In embodiments, the graphics driver may comprise a peripheral component interconnect (PCI) Express graphics card.

In various embodiments, any one or more of the components shown in the system 700 may be integrated. For example, the platform 702 and the content services device(s) 730 may be integrated, or the platform 702 and the content delivery device(s) 740 may be integrated, or the platform 702, the content services device(s) 730, and the content delivery device(s) 740 may be integrated, for example. In various embodiments, the platform 702 and the display 720 may be an integrated unit. The display 720 and content service device(s) 730 may be integrated, or the display 720 and the content delivery device(s) 740 may be integrated, for example. These examples are not meant to limit the embodiments.

In various embodiments, system 700 may be implemented as a wireless system, a wired system, or a combination of both. When implemented as a wireless system, system 700 may include components and interfaces suitable for communicating over a wireless shared media, such as one or more antennas, transmitters, receivers, transceivers, amplifiers, filters, control logic, and so forth. An example of wireless shared media may include portions of a wireless spectrum, such as the RF spectrum and so forth. When implemented as a wired system, system 700 may include components and interfaces suitable for communicating over wired communications media, such as input/output (I/O) adapters, physical connectors to connect the I/O adapter with a corresponding wired communications medium, a network interface card (NIC), disc controller, video controller, audio controller, and so forth. Examples of wired communications media may include a wire, cable, metal leads, printed circuit board (PCB), backplane, switch fabric, semiconductor material, twisted-pair wire, co-axial cable, fiber optics, and so forth.

The platform 702 may establish one or more logical or physical channels to communicate information. The information may include media information and control information. Media information may refer to any data representing content meant for a user. Examples of content may include, for example, data from a voice conversation, videoconference, streaming video, electronic mail ("email") message, voice mail message, alphanumeric symbols, graphics, image, video, text and so forth. Data from a voice conversation may be, for example, speech information, silence periods, background noise, comfort noise, tones and so forth. Control information may refer to any data representing commands, instructions or control words meant for an automated system. For example, control information may be used to route media information through a system, or instruct a node to process the media information in a predetermined manner. The embodiments, however, are not limited to the elements or in the context shown or described in FIG. 6.

In one example, the system 700 may include logic (e.g., logic instructions, configurable logic, fixed-functionality logic hardware, etc.) configured to implement any of the herein mentioned processes including, for example, detecting a material, extracting a material, characterizing a material, processing data, and so on. For example, the system 700 may include logic to implement the image device 12 (FIG. 1), the apparatus 20 (FIG. 1), the IR images 56, 62, 66, 66', 70 (FIGS. 2A-2E), the IR images 74a-74c and/or the waveforms 78a-78c (FIG. 3), the depth camera 80 and/or the waveforms 84, 92-96 (FIG. 4), and/or the method 100 (FIG. 5), already discussed.

Figure 7:
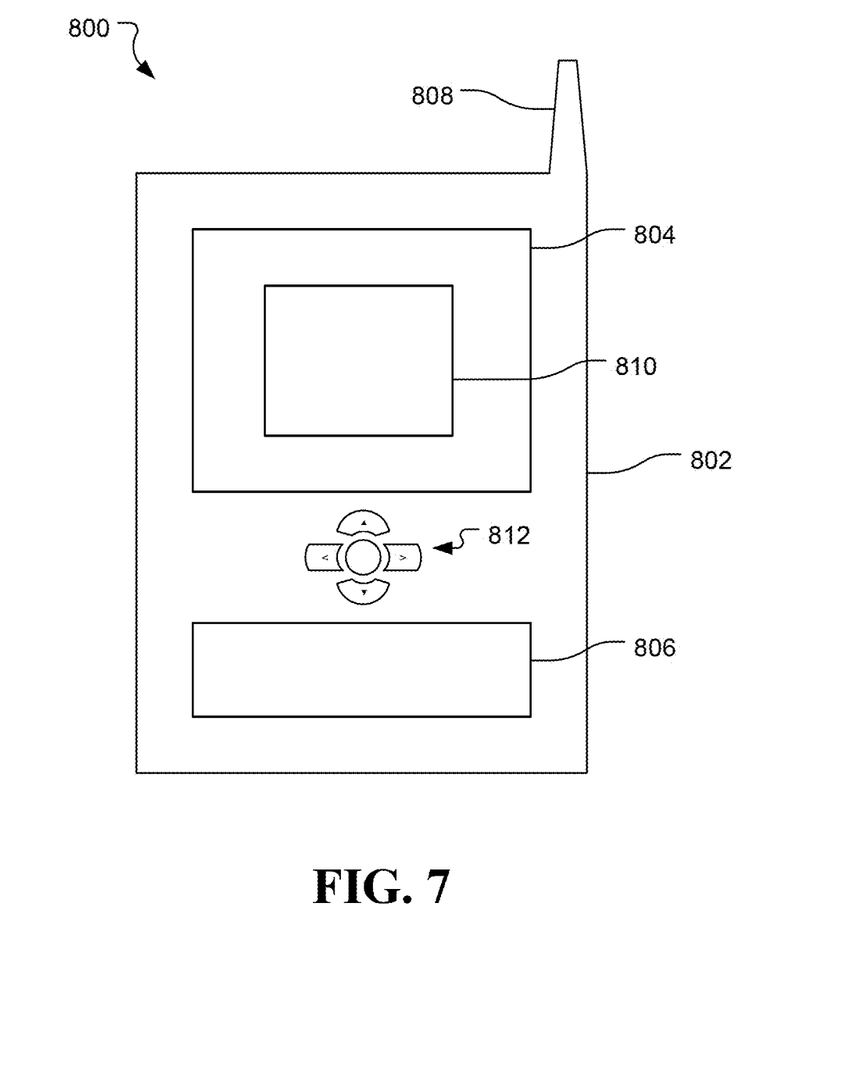
FIG. 7 is a block diagram of an example of a system having a small form factor according to an embodiment.

As described above, the system 700 may be embodied in varying physical styles or form factors. FIG. 7 illustrates embodiments of a small form factor device 800 in which the system 700 may be embodied. In embodiments, for example, the device 800 may be implemented as a mobile computing device having wireless capabilities. A mobile computing device may refer to any device having a processing system and a mobile power source or supply, such as one or more batteries, for example.

As described above, examples of a mobile computing device may include a personal computer (PC), laptop computer, ultra-laptop computer, tablet, touch pad, portable computer, handheld computer, palmtop computer, personal digital assistant (PDA), cellular telephone, combination cellular telephone/PDA, television, smart device (e.g., smart phone, smart tablet or smart television), mobile internet device (MID), messaging device, data communication device, and so forth.

Examples of a mobile computing device also may include computers that are arranged to be worn by a person, such as a wrist computer, finger computer, ring computer, eyeglass computer, belt-clip computer, arm-band computer, shoe computers, clothing computers, and other wearable computers. In embodiments, for example, a mobile computing device may be implemented as a smart phone capable of executing computer applications, as well as voice communications and/or data communications. Although some embodiments may be described with a mobile computing device implemented as a smart phone by way of example, it may be appreciated that other embodiments may be implemented using other wireless mobile computing devices as well. The embodiments are not limited in this context.

As shown in FIG. 7, the device 800 may comprise a housing 802, a display 804, an input/output (I/O) device 806, and an antenna 808. The device 800 also may comprise navigation features 812. The display 804 may comprise any suitable display unit for displaying information appropriate for a mobile computing device. The I/O device 806 may comprise any suitable I/O device for entering information into a mobile computing device. Examples for the I/O device 806 may include an alphanumeric keyboard, a numeric keypad, a touch pad, input keys, buttons, switches, rocker switches, microphones, speakers, voice recognition device and software, and so forth. Information also may be entered into the device 800 by way of microphone. Such information may be digitized by a voice recognition device. The embodiments are not limited in this context.

ADDITIONAL NOTES AND EXAMPLES

Example 1 may include a system to characterize a material comprising an image device including, an emitter to emit uniform infrared (IR) radiation that is to be converted to non-uniform IR radiation having a spatial IR pattern, and a capturer to capture non-uniform IR radiation that is to result from an interaction with a material, a pattern receiver to receive an IR pattern corresponding to non-uniform IR radiation that is to result from an interaction with a translucent material, and a characterizer to make a characterization of the translucent material based on the IR pattern, wherein the characterization is to differentiate the translucent material from one or more other translucent materials.

Example 2 may include the system of Example 1, further including one or more of a segmenter to segment an IR pattern, wherein the IR pattern that is to be segmented is to include an adjusted IR pattern, or a mixer to remix two or more segmented IR patterns into an output image.

Example 3 may include the system of any one of Examples 1 to 2, wherein the characterizer is to include one or more of, a detector to detect whether the translucent material is present in a three-dimensional space based on the IR pattern, or a classifier to classify the translucent material as a specific translucent material based on the IR pattern.

Example 4 may include an apparatus to characterize a material comprising a pattern receiver to receive an IR pattern corresponding to non-uniform IR radiation that is to result from an interaction with a translucent material, and a characterizer to make a characterization of the translucent material based on the IR pattern, wherein the characterization is to differentiate the translucent material from one or more other translucent materials.

Example 5 may include the apparatus of Example 4, further including a segmenter to segment an IR pattern based on a material optical property threshold, wherein the IR pattern that is to be segmented is to include an adjusted IR pattern, and wherein the material optical property threshold is to include a scattering threshold, and a mixer to remix two or more segmented IR patterns into an output image, wherein the mixer is to apply a weight to at least one of the two or more segmented IR patterns to further distinguish between translucent materials in the output image.

Example 6 may include the apparatus of any one of Examples 1 to 5, wherein the characterizer is to include a detector to detect whether the translucent material is present in a three-dimensional space based on the IR pattern.

Example 7 may include the apparatus of any one of Examples 1 to 6, wherein the detector is to utilize one or more of a raw IR pattern or an adjusted IR pattern to detect whether the translucent material is present, wherein the adjusted IR pattern is be an output of a convolution on the raw IR pattern.

Example 8 may include the apparatus of any one of Examples 1 to 7, wherein the characterizer is to include a classifier to classify the translucent material as a specific translucent material based on the IR pattern.

Example 9 may include the apparatus of any one of Examples 1 to 8, wherein the classifier is to, classify the one or more other translucent materials as a specific translucent material, and classify one or more materials as a non-translucent material.

Example 10 may include the apparatus of any one of Examples 1 to 9, wherein the classifier is to determine a material optical property of the translucent material to classify the translucent material as the specific translucent material.

Example 11 may include at least one computer readable storage medium comprising a set of instructions, which when executed by a processor, cause the processor to receive an IR pattern corresponding to non-uniform IR radiation that is to result from an interaction with a translucent material, and make a characterization of the translucent material based on the IR pattern, wherein the characterization is to differentiate the translucent material from one or more other translucent materials.

Example 12 may include the at least one computer readable storage medium of Example 11, wherein the instructions, when executed, cause the processor to one or more of segment an IR pattern based on a material optical property threshold, wherein the IR pattern that is to be segmented is to include an adjusted IR pattern, and wherein the material optical property threshold is to include a scattering threshold, remix two or more segmented IR patterns into an output image, or apply a weight to at least one of the two or more segmented IR patterns to further distinguish between translucent materials in the output image.

Example 13 may include the at least one computer readable storage medium of any one of Examples 11 to 12, wherein the instructions, when executed, cause the processor to detect whether the translucent material is present in a three-dimensional space based on the IR pattern.

Example 14 may include the at least one computer readable storage medium of any one of Examples 11 to 13, wherein the instructions, when executed, cause the processor to utilize one or more of a raw IR pattern or an adjusted IR pattern to detect whether the translucent material is present, wherein the adjusted IR pattern is be an output of a convolution on the raw IR pattern.

Example 15 may include the at least one computer readable storage medium of any one of Examples 11 to 14, wherein the instructions, when executed, cause the processor to classify the translucent material as a specific translucent material based on the IR pattern.

Example 16 may include the at least one computer readable storage medium of any one of Examples 11 to 15, wherein the instructions, when executed, cause the processor to one or more of, classify the one or more other translucent materials as a specific translucent material, or classify one or more materials as a non-translucent material.

Example 17 may include the at least one computer readable storage medium of any one of Examples 11 to 16, wherein the instructions, when executed, cause the processor to determine a material optical property of the translucent material to classify the translucent material as the specific translucent material.

Example 18 may include a method to characterize a material comprising receiving an IR pattern corresponding to non-uniform IR radiation that results from an interaction with a translucent material, and making a characterization of the translucent material based on the IR pattern, wherein the characterization differentiates the translucent material from one or more other translucent materials.

Example 19 may include the method of Example 18, further including one or more of segmenting an IR pattern based on a material optical property threshold, wherein the IR pattern that is segmented includes an adjusted IR pattern, and wherein the material optical property threshold includes a scattering threshold, remixing two or more segmented IR patterns into an output image, or applying a weight to at least one of the two or more segmented IR patterns to further distinguish between translucent materials in the output image.

Example 20 may include the method of any one of Examples 18 to 19, further including detecting whether the translucent material is present in a three-dimensional space based on the IR pattern.

Example 21 may include the method of any one of Examples 18 to 20, further including utilizing one or more of a raw IR pattern or an adjusted IR pattern to detect whether the translucent material is present, wherein the adjusted IR pattern is an output of a convolution on the raw IR pattern.

Example 22 may include the method of any one of Examples 18 to 21, further including classifying the translucent material as a specific translucent material based on the IR pattern.

Example 23 may include the method of any one of Examples 18 to 22, further including one or more of classifying the one or more other translucent materials as a specific translucent material, or classifying one or more materials as a non-translucent material.

Example 24 may include the method of any one of Examples 18 to 23, further including determining a material optical property of the translucent material to classify the translucent material as the specific translucent material.

Example 25 may include an apparatus to characterize a material comprising means for performing the method of any one of Examples 18 to 24.

Thus, techniques described herein provide for characterizing a material. For example, embodiments may characterize surface characteristics based on IR patterns. In one example, capabilities of depth cameras are extended to retrieve surface characteristics in addition to 3D location and color which may be used to characterize surface textures, characterize materials, and so on. In this regard, translucent materials may be distinguished from other materials (e.g., from other translucent materials, other non-translucent materials, etc.) in a 3D space.

Embodiments may include, for example, recognizing distortion of IR patterns as a result interactions of emitted IR patterns with specific materials (e.g., some materials make an IR pattern appear blurred in different densities). The differences may be used to detect materials. For example, embodiments may separate skin from other material (without prior knowledge). Moreover, embodiments may extract surface characteristics in a relatively robust way (e.g., 60 Hz without optimization). For example, embodiments may provide relatively robust detection (less than 5 ms, using a standard off-the shelf laptop without optimization). Together with 3D scanning and reconstructions, embodiments may retrieve point clouds with material properties (without RGB). Thus, output images may incorporate 3D/depth data.

In particular, embodiments may detect real human skin and distinguish real human skin from other material, such as rubber from a prosthetic. Embodiments may further provide a relatively robust technique to distinguish synthetic (non-real) skin (e.g., less that 5 ms, using a standard off-the shelf laptop without optimization) as an extra layer of checking if real skin is present. For example, embodiments are able to separate "no object", "rubber hand", or "real hand" using a skin filter pipeline. To extend to other materials, the resolution of detected materials may be increased.

Embodiments may provide for splitting an output image and segmenting a high scattering part from a low scattering part. Embodiments may further remix the two images back into one visualization. For example, an apple may appear to be relatively bright in IR sue to reflectance. In addition, sub-surface scattering may allow the apple to glow in the dark (in IR). A hand holding the apple, however, may not reflect as much light as the apple and is scattering light. In this case, embodiments may separate and highlight the two (by using a threshold based on over-saturated pixels) and then remix the two together. Thus, embodiments may utilize scattering light effects of a non-uniform IR emitter to characterize surface materials. Notably, material properties may be extracted in addition to depth data using a depth camera.

Embodiments are applicable for use with all types of semiconductor integrated circuit ("IC") chips. Examples of these IC chips include but are not limited to processors, controllers, chipset components, programmable logic arrays (PLAs), memory chips, network chips, systems on chip (SoCs), SSD/NAND controller ASICs, and the like. In addition, in some of the drawings, signal conductor lines are represented with lines. Some may be different, to indicate more constituent signal paths, have a number label, to indicate a number of constituent signal paths, and/or have arrows at one or more ends, to indicate primary information flow direction. This, however, should not be construed in a limiting manner. Rather, such added detail may be used in connection with one or more exemplary embodiments to facilitate easier understanding of a circuit. Any represented signal lines, whether or not having additional information, may actually comprise one or more signals that may travel in multiple directions and may be implemented with any suitable type of signal scheme, e.g., digital or analog lines implemented with differential pairs, optical fiber lines, and/ or single-ended lines.

Example sizes/models/values/ranges may have been given, although embodiments are not limited to the same. As manufacturing techniques (e.g., photolithography) mature over time, it is expected that devices of smaller size could be manufactured. In addition, well known power/ground connections to IC chips and other components may or may not be shown within the figures, for simplicity of illustration and discussion, and so as not to obscure certain aspects of the embodiments. Further, arrangements may be shown in block diagram form in order to avoid obscuring embodiments, and also in view of the fact that specifics with respect to implementation of such block diagram arrangements are highly dependent upon the computing system within which the embodiment is to be implemented, i.e., such specifics should be well within purview of one skilled in the art. Where specific details (e.g., circuits) are set forth in order to describe example embodiments, it should be apparent to one skilled in the art that embodiments can be practiced without, or with variation of, these specific details. The description is thus to be regarded as illustrative instead of limiting.

The term "coupled" may be used herein to refer to any type of relationship, direct or indirect, between the components in question, and may apply to electrical, mechanical, fluid, optical, electromagnetic, electromechanical or other connections. In addition, the terms "first", "second", etc. may be used herein only to facilitate discussion, and carry no particular temporal or chronological significance unless otherwise indicated.

As used in this application and in the claims, a list of items joined by the term "one or more of" or "at least one of" may mean any combination of the listed terms. For example, the phrases "one or more of A, B or C" may mean A; B; C; A and B; A and C; B and C; or A, B and C. In addition, a list of items joined by the term "and so on" or "etc." may mean any combination of the listed terms as well any combination with other terms.

Those skilled in the art will appreciate from the foregoing description that the broad techniques of the embodiments can be implemented in a variety of forms. Therefore, while the embodiments have been described in connection with particular examples thereof, the true scope of the embodiments should not be so limited since other modifications will become apparent to the skilled practitioner upon a study of the drawings, specification, and following claims.

We claim:

1. A system comprising:
one or more of configurable logic hardware or fixed functionality logic hardware,
an image device, implemented in one or more of the configurable logic hardware or fixed functionality logic hardware, including,
an emitter to emit uniform infrared (IR) radiation that is to be converted to non-uniform IR radiation having a spatial IR pattern, and
a capturer to capture non-uniform IR radiation that is to result from an interaction with a material,
a pattern receiver, implemented in one or more of the configurable logic hardware or fixed functionality logic hardware, to receive an IR pattern corresponding to non-uniform IR radiation that is to result from an interaction with a translucent material, a segmenter, implemented in one or more of the configurable logic hardware or fixed functionality logic hardware, to segment the IR pattern based on a material optical property threshold, wherein the IR pattern that is to be segmented is to include an adjusted IR pattern, and wherein the material optical property threshold is to include a scattering threshold, a mixer, implemented in one or more of the configurable logic hardware or fixed functionality logic hardware, to remix two or more segmented IR patterns into an output image, wherein the mixer is to apply a weight to at least one of the two or more segmented IR patterns to further distinguish between translucent materials in the output image, and a characterizer, implemented in one or more of the configurable logic hardware or fixed functionality logic hardware, to make a characterization of the translucent material based on the IR pattern, wherein the characterization is to differentiate the translucent material from one or more other translucent materials.

2. The system of claim 1, wherein the characterizer is to include one or more of,
a detector to detect whether the translucent material is present in a three-dimensional space based on the IR pattern, or
a classifier to classify the translucent material as a specific translucent material based on the IR pattern.

3. An apparatus comprising:
one or more of configurable logic hardware or fixed functionality logic hardware,
a pattern receiver, implemented in one or more of the configurable logic hardware or fixed functionality logic hardware, to receive an IR pattern corresponding to non-uniform IR radiation that is to result from an interaction with a translucent material,
a segmenter, implemented in one or more of the configurable logic hardware or fixed functionality logic hardware, to segment the IR pattern based on a material optical property threshold, wherein the IR pattern that is to be segmented is to include an adjusted IR pattern, and wherein the material optical property threshold is to include a scattering threshold,
a mixer, implemented in one or more of the configurable logic hardware or fixed functionality logic hardware, to remix two or more segmented IR patterns into an output image, wherein the mixer is to apply a weight to at least one of the two or more segmented IR patterns to further distinguish between translucent materials in the output image, and
a characterizer, implemented in one or more of the configurable logic hardware or fixed functionality logic hardware, to make a characterization of the translucent material based on the IR pattern, wherein the characterization is to differentiate the translucent material from one or more other translucent materials.

4. The apparatus of claim 3, wherein the characterizer is to include a detector to detect whether the translucent material is present in a three-dimensional space based on the IR pattern.

5. The apparatus of claim 4, wherein the detector is to utilize one or more of a raw IR pattern or the adjusted IR pattern to detect whether the translucent material is present, and wherein the adjusted IR pattern is to be an output of a convolution on the raw IR pattern.

6. The apparatus of claim 3, wherein the characterizer is to include a classifier to classify the translucent material as a specific translucent material based on the IR pattern.

7. The apparatus of claim 6, wherein the classifier is to,
classify the one or more other translucent materials as a specific translucent material, and
classify one or more materials as a non-translucent material.

8. The apparatus of claim 6, wherein the classifier is to determine a material optical property of the translucent material to classify the translucent material as the specific translucent material.

9. At least one non-transitory computer readable storage medium comprising a set of instructions, which when executed by a processor, cause the processor to:
receive an IR pattern corresponding to non-uniform IR radiation that is to result from an interaction with a translucent material;
segment the IR pattern based on a material optical property threshold, wherein the IR pattern that is to be segmented is to include an adjusted IR pattern, and wherein the material optical property threshold is to include a scattering threshold;
remix two or more segmented IR patterns into an output image;
apply a weight to at least one of the two or more segmented IR patterns to further distinguish between translucent materials in the output image; and
make a characterization of the translucent material based on the IR pattern, wherein the characterization is to differentiate the translucent material from one or more other translucent materials.

10. The at least one non-transitory computer readable storage medium of claim 9, wherein the instructions, when executed, cause the processor to detect whether the translucent material is present in a three-dimensional space based on the IR pattern.

11. The at least one non-transitory computer readable storage medium of claim 10, wherein the instructions, when executed, cause the processor to utilize one or more of a raw IR pattern or the adjusted IR pattern to detect whether the translucent material is present, wherein the adjusted IR pattern is to be an output of a convolution on the raw IR pattern.

12. The at least one non-transitory computer readable storage medium of claim 9, wherein the instructions, when executed, cause the processor to classify the translucent material as a specific translucent material based on the IR pattern.

13. The at least one non-transitory computer readable storage medium of claim 12, wherein the instructions, when executed, cause the processor to one or more of:
classify the one or more other translucent materials as a specific translucent material; or
classify one or more materials as a non-translucent material.

14. The at least one non-transitory computer readable storage medium of claim 12, wherein the instructions, when executed, cause the processor to determine a material optical property of the translucent material to classify the translucent material as the specific translucent material.

15. A method comprising:
receiving an IR pattern corresponding to non-uniform IR radiation that results from an interaction with a translucent material;
segmenting the IR pattern based on a material optical property threshold, wherein the IR pattern that is segmented includes an adjusted IR pattern, and wherein the material optical property threshold includes a scattering threshold;

remixing two or more segmented IR patterns into an output image;

applying a weight to at least one of the two or more segmented IR patterns to further distinguish between translucent materials in the output image; and making a characterization of the translucent material based on the IR pattern, wherein the characterization differentiates the translucent material from one or more other translucent materials.

16. The method of claim 15, further including detecting whether the translucent material is present in a three-dimensional space based on the IR pattern.

17. The method of claim 16, further including utilizing one or more of a raw IR pattern or the adjusted IR pattern to detect whether the translucent material is present, wherein the adjusted IR pattern is an output of a convolution on the raw IR pattern.

18. The method of claim 17, further including classifying the translucent material as a specific translucent material based on the IR pattern.

19. The method of claim 18, further including one or more of:

classifying the one or more other translucent materials as a specific translucent material; or classifying one or more materials as a non-translucent material.

20. The method of claim 18, further including determining a material optical property of the translucent material to classify the translucent material as the specific translucent material.

* * * * *